United States Patent [19]

Geary

[11] Patent Number: 5,126,139
[45] Date of Patent: Jun. 30, 1992

[54] PASTE INSECTICIDAL COMPOSITIONS

[75] Inventor: Daniel C. Geary, Randolph Township, Morris County, N.J.

[73] Assignee: The Clorox Company, Oakland, Calif.

[21] Appl. No.: 626,660

[22] Filed: Dec. 12, 1990

Related U.S. Application Data

[63] Continuation-in-part of Ser. No. 441,796, Nov. 27, 1989, abandoned.

[30] Foreign Application Priority Data

Nov. 23, 1990 [AU] Australia .............................. 66940/90
Nov. 26, 1990 [KR] Rep. of Korea ..................... 90-19173

[51] Int. Cl.$^5$ ............................................ A01N 25/08
[52] U.S. Cl. ...................................... 424/410; 424/84; 424/405; 514/275
[58] Field of Search .................... 424/410, 84, 405; 514/275

[56] References Cited

U.S. PATENT DOCUMENTS

| | | | |
|---|---|---|---|
| 4,049,460 | 9/1977 | Broadbent | 424/84 |
| 4,152,436 | 5/1979 | Drabb | 514/275 |
| 4,845,103 | 7/1989 | Spaulding | 514/275 |
| 4,888,174 | 12/1989 | Farquharson | 424/405 |
| 4,919,935 | 4/1990 | Dorn | 424/405 |

*Primary Examiner*—Thurman K. Page
*Assistant Examiner*—William E. Benston, Jr.
*Attorney, Agent, or Firm*—Harry A. Pacini

[57] ABSTRACT

A paste insecticide bait to be contained in a pressurized container, for dispensing a semi-solid bead of bait in cracks, crevices and the like for destroying insects, in particular cockroaches, said composition comprising an oil-in-water emulsion of a pentadienone toxicant/fatty acid mixture in a corn syrup solution, together with oatmeal and, optionally, titanium oxide.

5 Claims, No Drawings

PASTE INSECTICIDAL COMPOSITIONS

This application is a continuation-in-part of application Ser. No. 07/441,796, filed Nov. 27, 1989, now abandoned.

This invention relates to an insecticidal paste composition in a pressurized dispensing package for the control of cockroaches, and a method for its use. More particularly, the invention relates to dispensable paste insecticidal compositions comprising a pentadienone hydrazone as a toxicant, a fatty acid, a lower alcohol, a dispersant, water, a base, oatmeal, a hydrocarbon propellant and optionally titanium dioxide.

Existing insecticidal consumer pressurized sprays rely on contact mode-of-action for mortality, give only short-term efficacy against cockroaches, and may be repellant to the insect. Some of these sprays will be vaporized completely and so affect only those insects which are contacted. Others may be deposited as a liquid on surfaces, so that such deposits will be runny on vertical or overhead surfaces, and on non-absorbent surfaces. Such liquid deposits will also be absorbed into absorbent surfaces such as wood or wallpaper. Thus, these sprays will have little, if any, residual activity.

In copending, commonly assigned application Ser. Nos. 07/441,594, filed Nov. 27, 1989 and 07/442,024, filed Nov. 27, 1989, are disclosed baits which can be dispensed from pressurized packages in the form of a foam or gel. These baits solved some of the problems inherent in contact spray baits. They are solid, have form and can be ingested by roaches.

They do not readily soak into porous surfaces. They may be spread along cracks and crevices. However, these foam and gel baits still have certain disadvantages. The foam bait is somewhat runny on vertical or overhead surfaces and also tends to collapse over a period of time. Although the 1 gel bait adheres to a surface and retains more bulk, it also may run under elevated temperature, e.g., in a hot room or in hot weather.

It was also found that sprays or collapsible foams that end up as a soft thin film are physically difficult for roaches to pick up for ingestion.

The present invention exploits the insects feeding behavior to administer the pesticide to the insect and provides a bulk residue of long-lasting effectiveness. The present invention further provides a stable formulation for pressurized packaging.

The novel insecticidal paste compositions of the invention are suitable for application within and around cockroach habitats. This type of application requires compositions which possess physical properties which make them suitable for application as a bead of material in corners and hard to reach places within structures which are inhabited by cockroaches.

Pressurized spray paste bait allows delivery of non-repellant, long-lasting, semi-solid insecticidal bait into structural cracks and voids that harbor cockroaches. This requires that the composition be sufficiently fluid to be dispensed from a pressurized package and to be deposited in a form which will retain sufficient bulk to be ingested by cockroaches over a period of time.

In copending, commonly assigned application Ser. No. 07/442,024, filed Nov. 27, 1989, was disclosed an aerosol foam composition. It has been found that although such foams are effective, they collapse to a thin film and this is not an ideal form for the cockroach to pick up with its mouth parts. Principally, such foam residues lacks sufficient bulk.

The paste bait formulation of the present invention retains its bulk for a longer time, thus making it easy for the roach to ingest. On the other hand, the paste is not dispensable as an aerosol, because of its higher viscosity. In the present application, the paste composition is dispensed from a sepro dispenser can (well known in the art) which has an internal bladder filled with the paste. The bladder is surrounded by an inert gas under pressure, e.g., carbon dioxide or nitrogen. Gas compresses the bladder to expel product when the container valve is opened.

The invention can be applied to residential as well as industrial cockroach infestations for long-term control. This invention provides a means of delivering a poison cockroach bait in viscous form in situations where solid or liquid forms are inappropriate. Many species of pest insects are susceptible to control by this invention. It is particularly useful against cockroaches when applied to cockroach habitats.

This invention has the following advantages over aerosol contact and residual sprays and current bait tray technology:

The preparation is non-repellant. There is a higher frequency of bait placement yielding more complete treatment and control. The bait material can be placed in closer proximity to harborages than standard bait trays permitting tailoring of the bait application to structural idiosyncracies. Thus, enhancing the frequency that foraging insects will encounter the bait. The bait material is delivered in such a form and remains in the delivered semi-solid form so as to be readily available for ingestion by insects. Supplying a non-drying, non-collapsing paste at least 1/16" to ¼" in diameter makes it easier for the roaches to pick up the bait for ingestion. Long term efficacy can be achieved.

The present paste bait composition comprises, for example, an oil-in-water emulsion of a toxicant/fatty acid mixture in a corn syrup solution also containing oatmeal. Representative ingredients and their relative amounts are set forth in Table I as follows:

TABLE I

| Ingredient | Preferred % by weight | Range |
|---|---|---|
| Methyl Paraben, USP | 0.20 | 0.15–0.25 |
| Glycerin, USP | 2.00 | 0.00–3.00 |
| Corn Syrup | 40.00 | 30.00–50.00 |
| Water Deionized | 24.00 | |
| Compound CL 217,300 | 2.00 | 0.25–2.50 |
| Oleic Acid | 8.00 | 1.00–10.00 |
| Isopropanol (91% by volume) | 4.00 | 0.00–5.00 |
| Propylparaben, USP | 0.15 | 0.10–0.20 |
| Polyoxyethylene (5) cetyl stearyl ether | 5.00 | 3.00–6.00 |
| Oatmeal | 14.00 | 5.00–18.00 |
| Potassium Hydroxide (45%) | 0.17 | 0.10–0.20 |

TABLE I

It has been found that the addition of oatmeal increases the attractiveness of the bait to roaches above that of baits using sugar alone. Oat Pro ® (a 44 micron fraction) is preferred because valve clogging in the pressurized container is eliminated and it makes suspension of the oatmeal in the final product easier.

Even though kill is excellent, the aesthetics of the finished product are expected to be very important to the consumer. The ideal product should be water white, so it is unnoticeable during the 3–6 months it remains in exposed areas. Not having that, in the alternative, a white product, rather than a yellow product, would be next in desirability.

The product could be made white in spite of the oatmeal by adding small but whitening-effective amounts of titanium dioxide, if sufficient amounts of fatty acid are present to cause yellowing of the product. If only equivalent weights of fatty acid are present to neutralize the pentadienone toxicant, the finished product is yellow, since the fatty acid/pentadienone salt itself is yellow in color at 55° C. or when cooled to room temperature. It was found that additions of the fatty acid/oleic acid, in excess of four times the equivalent weight of pentadienone eliminates the yellow color. The reason is not readily understood. However, fatty acid at the level of four times the equivalent provides whiteness at pH 5.5 up to 7.5 at which point the yellowness reappears. Above the pH of 7.5 further increases of fatty acid appear to have no effect on eliminating yellowness. Addition of a whitening-effective amount of titanium dioxide can aid to eliminate the yellow coloration at pH above about 7.5.

It has been found that this choice of fatty acid is important. Oleic acid results in solubilization of the pentadienone insecticide to give a liquid salt which remains liquid indefinitely at room temperature. This is true even if isopropanol (91% by volume) is not present. Solubilization and liquification also can be obtained when the pH is raised to 7 with a base, such as potassium hydroxide. It is extremely easy to emulsify the liquid salt at room temperature in aqueous phase by using just enough heat to liquefy the solid emulsifier (POE (5) cetyl stearyl ether).

In contrast, the stearic acid/pentadienone salt did not remain soluble at lower temperatures, e.g., 40° C. and could not provide a stable emulsion.

The pentadienone poison is an insecticide which is active as a stomach poison.

Pentadiene-3-one substituted amidinohydrazones are described by Tomcufcik, U.S. Pat. No. 3,878,201, as antimalarial and antitubercular agents. Lovell, U.S. Pat. No. 4,087,525 and 4,163,102 — the disclosures of which are incorporated herein by reference, describe the use of these compounds as insecticides. The insecticide compounds of the Lovell patents are generally represented by the formula:

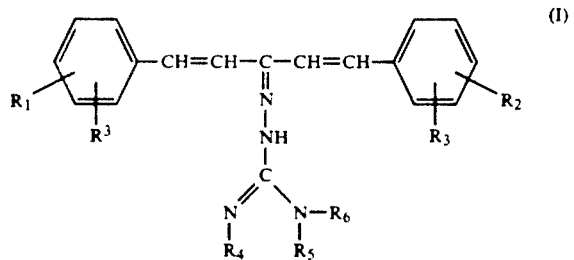
(I)

wherein $R_1$ and $R_2$ each represent hydrogen, halogen, the group $-CF_3$, $C_1-C_4$ alkyl, $C_1-C_4$ alkoxy, or $C_1-C_4$ alkylthio;

$R_3$ is hydrogen or methyl, provided that when $R_3$ is methyl both $R_1$ and $R_2$ are also methyl;

$R_4$ and $R_5$ represent hydrogen, $C_1-C_4$ alkyl or when taken together, an alkylene group of 2 to 6 carbon atoms, methyl or a phenylalkylene group of 2 to 6 carbon atoms of 1,2-cyclohexylene; and $R_6$ is hydrogen or $C_1-C_4$ alkyl; and salts Particularly useful compounds are those represented by the formula:

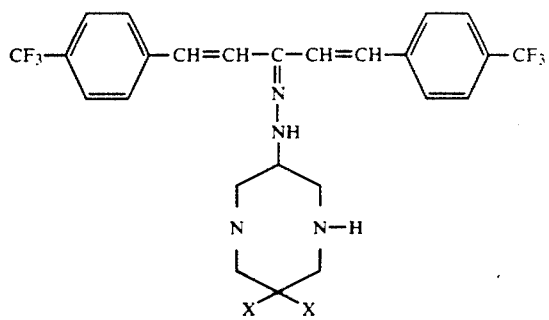

wherein X is hydrogen or methyl. The efficacy of the compounds represented by formulas (I) and (II) against a variety of Lepidopterous, Orthopterous, Dipterous and Hymenopterous insects is also described by Lovell.

However, the form and method of use described in these prior art patents is generally related to agricultural applications, where particulate baits are used and distributed over wide, open areas, and the types of bait system suggested therein are clearly not suitable for general household consumer use.

A pressurized dispensable paste bait formulation was prepared and evaluated as shown in the following Examples.

EXAMPLE I

A paste bait was prepared having the following composition by weight:

|  | Weight % | |
|---|---|---|
|  | A, B | C |
| Corn Syrup | 40.00 | 40.00 |
| Pentadienone (CL 217,300) | 2.00 | 2.00 |
| Oleic Acid | 8.00 | 8.00 |
| Isopropanol | 6.00 | 6.00 |
| Methyl Paraben | 0.20 | 0.20 |
| Polyoxyethylene (5) Stearyl Ether | 5.00 | 5.00 |
| Water | 9.50 | 9.50 |
| Oatmeal | 14.00[1] | 7.00[2] |
| Potassium hydroxide | 0.17 | 0.17 |
| Glycerin | 2.00 | 2.00 |
| Propyl Paraben | 0.15 | 0.15 |

[1]Two identical compositions were prepared except for the type of oatmeal. In Preparation A, hand ground oatmeal was used. In Preparation B, a commercially ground product, OATPRO' (ground 44 microns) was used.
[2]OATPRO$^R$ oatmeal.

EXAMPLE II

The paste baits of Example I were tested in the laboratory against German cockroaches and compared with a gel bait disclosed in commonly assigned, copending application Ser. No. 07/441,594, filed Nov. 27, 1989 and against solid bait in a feed station described in U.S. Pat. No. 4,563,836, issued Jan. 14, 1986.

Material and Methods

The compositions of Example I were tested against laboratory model infestations comprising populations of German cockroaches confined in test arenas and provided with harborage, water, and an abundant supply of alternate food. Test arenas consist of 18" square areas bounded by glass walls 6" high greased with a mixture of petrolatum and mineral oil to prevent cockroaches from escaping. Each arena contains a cardboard box (2.75×5.25×7.75 inches) harborage provided with an entrance slit and a liner of pleated corrugated cardboard strip (1.50×18") and a 2 ounce water bottle with paper towel wick. Harborage and water bottle are disposed against one wall of the arena. An alternate food supply of approximately 20 nuggets of PURINA ® Cat Chow is distributed around the harborage entrance. Populations of approximately 25 German cockroaches of mixed ages and both sexes are installed in each arena by random allocation of a representative sample drawn from a rearing facility. Cockroach populations are installed approximately four days prior to the introduction of bait treatments into the arenas. Arenas are maintained at room temperature (70-80° F.) throughout the test period.

Bait treatments are applied to model baseboards consisting of two 3×6' pieces of unfinished ¼" plywood glued along a long edge to form an L-shaped profile or to glass plates 6" square. Baits are applied at the rate of approximately 5 grams of product per arena. Bait treatments are assigned to arenas in a completely randomized manner.

Mortality of each arena is assessed seven days after the introduction of bait treatments. Cockroaches not responding with greater than one body-length of escape motion upon prodding of cerci by forceps are classified as dead. The results are shown in Table II below.

TABLE II

| Treat | Efficacy Test Results Mean Percent Reduction at Day 7 |
|---|---|
| Paste Bait 13355 with ground oatmeal | 89% |
| Paste Bait 13355 with OATPRO$^R$ | 89% |
| COMBAT Feeding Station 9490 | 89% |
| COMBAT Gel Bait 13581 | 79% |

We claim:

1. An insecticidal paste composition for application from a pressurized container for destroying cockroaches which comprises, by weight, 30% to 50% corn syrup, 0.25% to 2.5% of a pentadienone insecticide, 3% to 6% polyoxyethylene (5) cetyl stearyl ether, 0.10% to 0.2% of at least one antimicrobial agent, about 0% to 5% isopropanol, about 1% to 10% oleic acid, 15% to 30% water, 0.1% to 0.2% of a base, 1% to 5% polydimethyl siloxane, 0% to 3% glycerin, and 5% to 18% oatmeal.

2. The composition of claim 1 wherein said pentadienone is a compound of the formula:

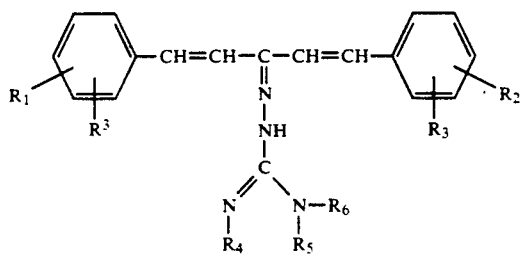

wherein
$R_1$ and $R_2$ each represent hydrogen, halogen, the group —$CF_3$, $C_1$-$C_4$ alkyl, $C_1$-$C_4$ alkoxy, or $C_1$-$C_4$ alkylthio;
$R_3$ is hydrogen or methyl, provided that when $R_3$ is methyl both $R_1$ and $R_2$ are
$R_4$ and $R_5$ represent hydrogen, $C_1$-$C_4$ alkyl or when taken together, an alkylene group of 2 to 6 carbon atoms, methyl or phenyl alkylene group of 2 to 6 carbon atoms of 2-cyclohexylene; and
$R_6$ is hydrogen or $C_1$-$C_4$ alkyl; and salts thereof.

3. The paste composition of claim 2 wherein said base is potassium hydroxide.

4. A method for destroying cockroaches which comprises dispensing the composition of claim 2 from a pressurized container and depositing said composition as a semi-solid bead of material along cracks and crevices of cockroach harborages.

5. The paste composition of claim 2 containing a whitening-effective amount of titanium dioxide.

* * * * *